United States Patent
Olson et al.

(10) Patent No.: US 9,107,989 B2
(45) Date of Patent: Aug. 18, 2015

(54) REDUCED PRESSURE WOUND DRESSING HAVING A WOUND CONTACT SURFACE WITH COLUMNAR PROTRUSIONS

(75) Inventors: Jonathan S. Olson, Austin, TX (US); Devin C. Ginther, Dripping Springs, TX (US); T. Blane Sanders, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 561 days.

(21) Appl. No.: 13/289,827

(22) Filed: Nov. 4, 2011

(65) Prior Publication Data

US 2012/0053539 A1    Mar. 1, 2012

Related U.S. Application Data

(63) Continuation of application No. 12/118,524, filed on May 9, 2008, now Pat. No. 8,057,447.

(60) Provisional application No. 60/928,644, filed on May 10, 2007.

(51) Int. Cl.
*A61F 13/00* (2006.01)
*A61M 1/00* (2006.01)
(Continued)

(52) U.S. Cl.
CPC ........ *A61M 1/0088* (2013.01); *A61F 13/00068* (2013.01); *A61F 13/0203* (2013.01); *A61F 13/512* (2013.01); *A61F 2013/00217* (2013.01)

(58) Field of Classification Search
CPC ............... A61F 13/00068; A61F 2013/00089; A61F 2013/00217; A61F 2013/00331; A61F 2013/00519; A61F 2013/0054
See application file for complete search history.

(56) References Cited

U.S. PATENT DOCUMENTS

| 1,355,846 A | 10/1920 | Rannells |
| 2,305,289 A | 12/1942 | Coburg |

(Continued)

FOREIGN PATENT DOCUMENTS

| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Leslie Deak
*Assistant Examiner* — Kai Weng

(57) ABSTRACT

A reduced pressure treatment system includes a distribution manifold having a backing substrate with a first side and a second side and a plurality of protrusions positioned on the first side of the backing substrate. Each of the protrusions includes a substantially circular cross-sectional shape and has a diameter of between about 0.1 and 2.0 millimeters, the backing substrate having a plurality of apertures formed therein to allow fluid communication between the first side and the second side opposite the first side. A reduced pressure source is fluidly connected to the apertures of the backing substrate to deliver the reduced pressure through the apertures, between the protrusions, and to a tissue site.

17 Claims, 4 Drawing Sheets

(51) Int. Cl.
*A61F 13/02* (2006.01)
*A61F 13/512* (2006.01)

(56) References Cited

U.S. PATENT DOCUMENTS

| | | | |
|---|---|---|---|
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,026,874 A | 3/1962 | Stevens | |
| 3,066,672 A | 12/1962 | Crosby, Jr. et al. | |
| 3,089,492 A | 5/1963 | Owens | |
| 3,142,298 A | 7/1964 | Koski et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,992,162 A * | 11/1976 | Gewiss | 428/604 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,250,882 A | 2/1981 | Adair | |
| 4,256,109 A | 3/1981 | Nichols | |
| 4,261,360 A | 4/1981 | Perez | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,342,745 A | 8/1982 | Mirkovitch | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,444,545 A | 4/1984 | Sanders et al. | |
| 4,465,485 A | 8/1984 | Kashmer et al. | |
| 4,468,219 A | 8/1984 | George et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,533,352 A | 8/1985 | Van Beek et al. | |
| 4,534,356 A | 8/1985 | Papadakis | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,614,183 A | 9/1986 | McCracken et al. | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,795,435 A | 1/1989 | Steer et al. | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,930,997 A | 6/1990 | Bennett | |
| 4,941,882 A | 7/1990 | Ward et al. | |
| 4,953,565 A | 9/1990 | Tachibana et al. | |
| 4,969,880 A | 11/1990 | Zamierowski | |
| 4,979,944 A | 12/1990 | Luzsicza | |
| 4,985,019 A | 1/1991 | Michelson | |
| 5,013,300 A | 5/1991 | Williams | |
| 5,034,006 A | 7/1991 | Hosoda et al. | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,195,977 A | 3/1993 | Pollitt | |
| 5,215,522 A | 6/1993 | Page et al. | |
| 5,232,453 A | 8/1993 | Plass et al. | |
| 5,260,066 A | 11/1993 | Wood et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,449,347 A | 9/1995 | Preen et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,678,564 A | 10/1997 | Lawrence et al. | |
| 5,735,833 A | 4/1998 | Olson | |
| 5,762,640 A | 6/1998 | Kajiwara et al. | |
| 5,776,119 A | 7/1998 | Bilbo et al. | |
| 5,827,246 A | 10/1998 | Bowen | |
| 5,902,260 A | 5/1999 | Gilman et al. | |
| 5,941,859 A | 8/1999 | Lerman | |
| 6,051,747 A | 4/2000 | Lindqvist et al. | |
| 6,071,267 A | 6/2000 | Zamierowski | |
| 6,080,243 A | 6/2000 | Insley et al. | |
| 6,135,116 A | 10/2000 | Vogel et al. | |
| 6,142,982 A | 11/2000 | Hunt | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,458,109 B1 | 10/2002 | Henley et al. | |
| 6,471,982 B1 | 10/2002 | Lydon et al. | |
| 6,482,491 B1 * | 11/2002 | Samuelsen et al. | 428/40.1 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,566,575 B1 | 5/2003 | Stickels et al. | |
| 6,572,594 B2 | 6/2003 | Satterfield et al. | |
| 6,660,484 B2 | 12/2003 | Charych et al. | |
| 6,682,506 B1 | 1/2004 | Navarro | |
| 6,695,823 B1 | 2/2004 | Lina et al. | |
| 6,752,794 B2 * | 6/2004 | Lockwood et al. | 604/313 |
| 6,814,079 B2 | 11/2004 | Heaton et al. | |
| 7,070,584 B2 | 7/2006 | Johnson et al. | |
| 7,117,869 B2 | 10/2006 | Heaton et al. | |
| 7,195,624 B2 | 3/2007 | Lockwood et al. | |
| 7,273,054 B2 | 9/2007 | Heaton et al. | |
| 7,276,051 B1 | 10/2007 | Henley et al. | |
| 7,316,672 B1 | 1/2008 | Hunt | |
| 7,344,512 B2 | 3/2008 | Yamazaki et al. | |
| 7,381,859 B2 | 6/2008 | Hunt et al. | |
| 7,396,339 B2 | 7/2008 | Britto et al. | |
| 7,651,484 B2 | 1/2010 | Heaton et al. | |
| 7,670,323 B2 | 3/2010 | Hunt et al. | |
| 7,846,141 B2 | 12/2010 | Weston | |

(56) References Cited

U.S. PATENT DOCUMENTS

| | | |
|---|---|---|
| 7,867,206 B2 | 1/2011 | Lockwood et al. |
| 7,886,746 B2 | 2/2011 | Heaton et al. |
| 8,057,447 B2 | 11/2011 | Olson et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0161346 A1 | 10/2002 | Lockwood et al. |
| 2003/0108587 A1* | 6/2003 | Orgill et al. .......... 424/423 |
| 2004/0073151 A1 | 4/2004 | Weston |
| 2004/0127836 A1 | 7/2004 | Sigurjonsson et al. |
| 2005/0004534 A1 | 1/2005 | Lockwood |
| 2005/0261642 A1 | 11/2005 | Weston |
| 2005/0283105 A1 | 12/2005 | Heaton et al. |
| 2007/0118096 A1 | 5/2007 | Smith et al. |
| 2008/0275409 A1 | 11/2008 | Kane et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 3907007 | 9/1990 |
| DE | 43 06 478 A1 | 9/1994 |
| DE | 295 04 378 U1 | 10/1995 |
| EP | 0080179 A1 | 11/1982 |
| EP | 0100148 A1 | 2/1984 |
| EP | 0117632 A2 | 9/1984 |
| EP | 0161865 A2 | 11/1985 |
| EP | 0300621 | 1/1989 |
| EP | 0358302 A2 | 3/1990 |
| EP | 0619105 A1 | 4/1994 |
| EP | 018967 B1 | 8/2004 |
| GB | 692578 | 6/1953 |
| GB | 1579860 | 4/1976 |
| GB | 2125296 A | 3/1984 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2227035 A | 10/1994 |
| GB | 2 333 965 A | 8/1999 |
| GB | 2 329 127 B | 8/2000 |
| JP | 56-500360 | 3/1981 |
| JP | A 59-141943 | 8/1984 |
| JP | 4129536 | 4/1992 |
| JP | 2005312343 | 10/2005 |
| JP | 2006325532 | 7/2006 |
| RU | 2242956 | 12/2004 |
| SG | 71559 | 4/2002 |
| WO | WO 80/02182 | 10/1980 |
| WO | WO 87/04626 | 8/1987 |
| WO | WO 90/010424 | 9/1990 |
| WO | WO 90/11795 | 10/1990 |
| WO | WO 93/09727 | 5/1993 |
| WO | WO9417765 | 8/1994 |
| WO | WO 94/20041 | 9/1994 |
| WO | WO 95/17912 | 7/1995 |
| WO | WO 96/05873 | 2/1996 |
| WO | WO 97/18007 | 5/1997 |
| WO | WO 99/13793 | 3/1999 |
| WO | WO 2001/034223 | 5/2001 |
| WO | WO 2001/037922 | 5/2001 |
| WO | WO 01/85248 | 11/2001 |
| WO | WO 01/89431 | 11/2001 |
| WO | WO 03/045492 | 6/2003 |
| WO | WO 03/057070 | 7/2003 |
| WO | WO2004018020 | 3/2004 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61(1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A,, et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

(56) References Cited

OTHER PUBLICATIONS

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Ð ukić, Ž. Maksimović, Ð . Radak, and P. Peška, "Vacuum Therapy in the Treatment of Peripheral Blood Vessels," *Timok Medical Journal 11* (1986), pp. 161-164 (certified translation).
F.E. Johnson, "An Improved Technique for Skin Graft Placement Using a Suction Drain," *Surgery, Gynecology, and Obstetrics 159* (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967 (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, " *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909 , pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Notice of Opposition date mailed Apr. 28, 2010 in European Patent No. 1772160.
International Search Report and Written Opinion date mailed Aug. 4, 2008 for PCT/US2008/063305.
Notice of Opposition date mailed Oct. 13, 2010 to European Patent No. 1637088.
Teder, et al., "Continuous Wound Irrigation in the Pig" Journal of Investigative Surgery, vol. 3, pp. 399-407; 1990 (opp-459).
Response filed Feb. 14, 2011 to Smith and Nephew's Opposition for EP Patent No. 1637088.
Kane et al "Controlled Induction of Distributed Microdeformation in Wounded Tissue via a Microchamber Array Dressing", pp. 333-340; Journal of Biomedical Materials Research; Nov. 2010, vol. 95A, Issue 2.
Quayle Office Action dated Nov. 16, 2001 for U.S. Appl. No. 09/613,497.
Response filed Mar. 19, 2004 for U.S. Appl. No. 09/613,497.
Non-Final Office Action dated Jul. 13, 2004 for U.S. Appl. No. 09/613,497.
Response filed Jan. 12, 2005 for U.S. Appl. No. 09/613,497.
Non-Final Office Action dated Feb. 7, 2006 for U.S. Appl. No. 09/613,497.
Response filed Jul. 8, 2006 for U.S. Appl. No. 09/613,497.
Notice of Non-Compliant dated Jul. 14, 2006 for U.S. Appl. No. 09/613,497.
Response filed Aug. 10, 2006 for U.S. Appl. No. 09/613,497.
Notice of Allowance and Fee(s) Due dated Oct. 13, 2006 for U.S. Appl. No. 09/613,497.
Request for Continued Examination dated Feb. 26, 2007 for U.S. Appl. No. 09/613,497.
Notice of Allowance and Fee(s) Due dated Apr. 5, 2007 for U.S. Appl. No. 09/613,497.
Request for Continued Examination dated Jul. 9, 2007 for U.S. Appl. No. 09/613,497.
Response filed Jul. 19, 2007 for U.S. Appl. No. 09/613,497.
Notice of Allowance and Fee(s) Due dated Aug. 6, 2007 for U.S. Appl. No. 09/613,497.
Non-Final Office Action dated Oct. 18, 2007 for U.S. Appl. No. 11/713,485.
Response filed Mar. 18, 2008 for U.S. Appl. No. 11/713,485.
Non-Final Office Action dated Jun. 26, 2008 for U.S. Appl. No. 11/713,485.
Response filed Sep. 8, 2008 for U.S. Appl. No. 11/713,485.
Non-Final office action Dec. 10, 2008 for U.S. Appl. No. 11/713,485.
Response filed Mar. 4, 2009 for U.S. Appl. No. 11/713,485.
Final Office Action date mailed May 19, 2009 for U.S. Appl. No. 11/713,485.
Interview Summary date mailed Jul. 17, 2009 for U.S. Appl. No. 11/713,485.
RCE/Response filed Aug. 21, 2009 for U.S. Appl. No. 11/713,485.
Notice of Allowance date mailed Nov. 30, 2009 for U.S. Appl. No. 11/713,485.
Restriction Requirement date mailed Nov. 22, 2011 for U.S. Appl. No. 12/711,182.
Response filed Dec. 16, 2011 for U.S. Appl. No. 12/711,182.
Non-final Office Action date mailed May 19, 2009 for U.S. Appl. No. 11/545,321.
Response filed Nov. 19, 2009 for U.S. Appl. No. 11/545,321.
Final Action date mailed Mar. 4, 2010 for U.S. Appl. No. 11/545,321.
Response filed May 4, 2010 for U.S. Appl. No. 11/545,321.
Notice of Allowance date mailed Jun. 11, 2010 for U.S. Appl. No. 11/545,321.
RCE/Response filed Sep. 3, 2010 for U.S. Appl. No. 11/545,321.
Notice of Allowance date mailed Nov. 24, 2010 for U.S. Appl. No. 11/545,321.
Non-Final Office Action dated Jun. 12, 2008 for U.S. Appl. No. 11/702,822.
Response filed Jul. 14, 2008 for U.S. Appl. No. 11/702,822.
Non-Final Office Action dated Aug. 26, 2008 for U.S. Appl. No. 11/702,822.
Response filed Nov. 13, 2008 for U.S. Appl. No. 11/702,822.
Notice of Allowance dated Apr. 16, 2009 for U.S. Appl. No. 11/702,822.
RCE filed Jun. 4, 2009 for U.S. Appl. No. 11/702,822.
Notice of Allowance date mailed Aug. 24, 2009 for U.S. Appl. No. 11/702,822.
Notice of Allowance date mailed Sep. 14, 2009 for U.S. Appl. No. 11/702,822.
Notice of Allowance date mailed Dec. 3, 2009 for U.S. Appl. No. 11/702,822.
Restriction Requirement date mailed Dec. 15, 2011 for U.S. Appl. No. 12/650,318.
Restriction Requirement date mailed Sep. 27, 2010 for U.S. Appl. No. 12/118,524.
Response filed Oct. 20, 2010 for U.S. Appl. No. 12/118,524.
Non-Final Office Action date mailed Jan. 5, 2011 for U.S. Appl. No. 12/118,524.
Interview Summary date mailed Feb. 17, 2011 for U.S. Appl. No. 12/118,524.
Response filed Apr. 5, 2011 for U.S. Appl. No. 12/118,524.
Interview Summary date mailed May 20, 2011 for U.S. Appl. No. 12/118,524.
Notice of Allowance date mailed Jul. 11, 2011 for U.S. Appl. No. 12/118,524.

\* cited by examiner

REDUCED PRESSURE WOUND DRESSING HAVING A WOUND CONTACT SURFACE WITH COLUMNAR PROTRUSIONS

CROSS-REFERENCE TO RELATED APPLICATIONS

This application is a continuation of U.S. application Ser. No. 12/118,524, filed May 9, 2008 now U.S. Pat. No. 8,057,447, which claims the benefit of U.S. Provisional Application No. 60/928,644, filed May 10, 2007, both of which are hereby incorporated by reference.

BACKGROUND

1. Field of the Invention

The present invention relates generally to tissue treatment systems and in particular to distribution manifolds for wound treatment.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad often is incorporated into a dressing having other components that facilitate treatment.

Distribution manifolds for delivering reduced pressure treatment are also commonly referred to as reduced pressure dressings, or in the case of treatment of a wound, wound dressings. Such dressings are characterized by structural features that allow fluid flow through the material. For example, one material that is often used as a wound dressing is reticulated, open-cell polyurethane foam. The foam includes a plurality of interconnected pores that allow fluid flow throughout the foam. When a reduced pressure is applied to one area of the foam, this reduced pressure is quickly distributed to other areas of the foam and is easily transmitted to tissues adjacent the foam. One problem with open-cell foams and similar materials is tissue in-growth, which prevents easy removal of the foam following treatment. For open cells foams with pore sizes on the order of 100-1000 microns, in-growth of tissue may occur relatively quickly. As the new tissue enters the pores or cells of the foam, the foam acts as a lattice, and tissue grows within the pores and around the walls that form the perimeter of the pores. This effectively attaches the foam to the tissue site, and the foam must be forcibly removed by tearing the new tissue and breaking any bonds that have formed between the tissue and the foam. Not only is this detrimental to the healing process, but the tearing of this tissue may cause discomfort to the patient.

One way to circumvent the problem of tissue in-growth is to increase the frequency of dressing changes. If new dressings are applied with increased frequency, there is less tissue in-growth, and thus less disruption of new tissue upon removing the old dressing. One downside to increased dressing changes is the increased costs associated with materials (i.e. new dressings) and labor. Changing a dressing is labor intensive and diverts the attention of medical personnel from other important tasks. Increased dressing changes also result in more aggravation to patients and their wounds.

SUMMARY

The problems presented by existing reduced pressure treatment systems are solved by the systems and methods of the illustrative embodiments described herein. In one embodiment, a reduced pressure treatment system is provided and includes a distribution manifold including a backing substrate and a plurality of protrusions positioned on a first side of the backing substrate with each of the protrusions having substantially circular cross-sectional shape and having a diameter of between about 0.1 and 2.0 millimeters. The backing substrate has a plurality of apertures formed therein to allow fluid communication between the first side and a second side opposite the first side. A reduced pressure source fluidly connected to the apertures of the backing substrate to deliver the reduced pressure through the apertures, between the protrusions, and to a tissue site.

In another embodiment, a reduced pressure treatment system is provided and includes a distribution manifold including a backing substrate and a plurality of protrusions positioned on a first side of the backing substrate, each of the protrusions having a substantially polygonal cross-sectional shape and having a width of between about 0.1 and 2.0 millimeters. The backing substrate has a plurality of apertures formed therein to allow fluid communication between the first side and a second side opposite the first side. A reduced pressure source fluidly connected to the apertures of the backing substrate to deliver the reduced pressure through the apertures, between the protrusions, and to a tissue site.

In another embodiment, a reduced pressure treatment system is provided and includes a distribution manifold including a backing substrate and a plurality of columnar voids positioned on a first side of the backing substrate, each of the columnar voids having substantially polygonal cross-sectional shape and having a width of between about 0.1 and 2.0 millimeters.

In another embodiment, a reduced pressure treatment system is provided and includes a distribution manifold including a backing substrate and a plurality of protrusions positioned on a first side of the backing substrate, each of the protrusions having substantially circular cross-sectional shape and tapering inward from the base at which the protrusions meet the backing substrate. The backing substrate has a plurality of apertures formed therein to allow fluid communication between the first side and a second side opposite the first side. A reduced pressure source is fluidly connected to the apertures of the backing substrate to deliver the reduced pressure through the apertures, between the protrusions, and to a tissue site.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The several embodiments of the present invention described herein are provided to assist in the healing of wounds and generation of new tissue. Reduced pressure therapy is administered to patients with a reduced pressure delivery system. This form of advanced wound healing therapy can be readily integrated into a clinician's wound healing procedures. The therapy optimizes patient care and decreases costs associated with treatment of patients having traumatic and chronic wounds. With the innovative embodiments of the reduced pressure delivery system described herein, reduced pressure therapy can be administered either in the hospital, in community settings such as assisted living complexes and convalescence homes, or in the home.

Reduced pressure delivery to a wound or tissue site promotes wound healing and/or tissue growth by removing infectious materials and other fluids from the wound or tissue site. Reduced pressure treatment further promotes tissue growth by imposing forces on the tissue, thereby causing micro-deformation of the tissue, which is believed to contribute to the development of granulation tissue at the tissue site. The forces imposed on the tissue site by the delivery of reduced pressure further encourage improved blood flow to the tissue site, which further assists in the growth of new tissue.

Figure 1:
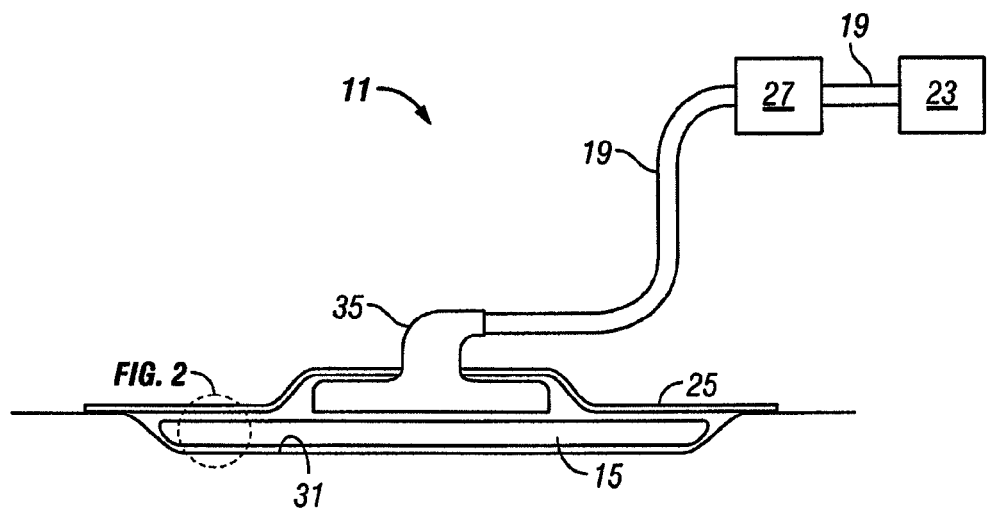
FIG. 1 illustrates a reduced pressure treatment system 11 according to an embodiment of the present invention.

Referring to FIG. 1, a reduced pressure treatment system 11 according to an embodiment of the present invention includes a reduced pressure dressing, or distribution manifold 15 fluidly connected to a reduced pressure conduit 19. The reduced pressure conduit 19 is fluidly connected to a reduced pressure source 23 such as a vacuum pump or another source of suction. The distribution manifold 15 is placed against a tissue site 31 of a patient and is used to distribute a reduced pressure provided by the reduced pressure source 23. Typically, reduced pressure is maintained at the tissue site by placing an impermeable or semi-permeable cover 25 over the distribution manifold 15 and the tissue site 31. The reduced pressure also serves to draw wound exudates and other fluids from the tissue site 31. A canister 27 may be fluidly connected to the reduced pressure conduit 19 and disposed between the wound dressing 15 and the reduced pressure source 23 to collect the fluids drawn from the tissue site 31. A distribution adapter 35 may be connected to the reduced pressure conduit 19 and positioned on the distribution manifold 15 to aid in distributing the reduced pressure to the distribution manifold 15.

Figure 2:
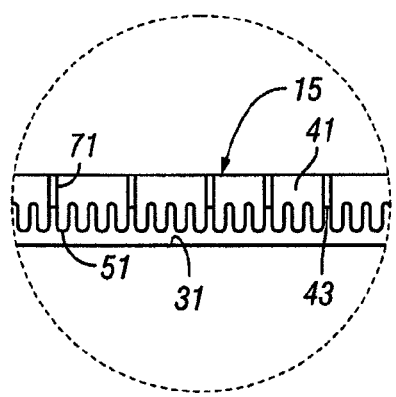
FIG. 2 illustrates the distribution manifold according to an embodiment of the present invention.
Figure 3:
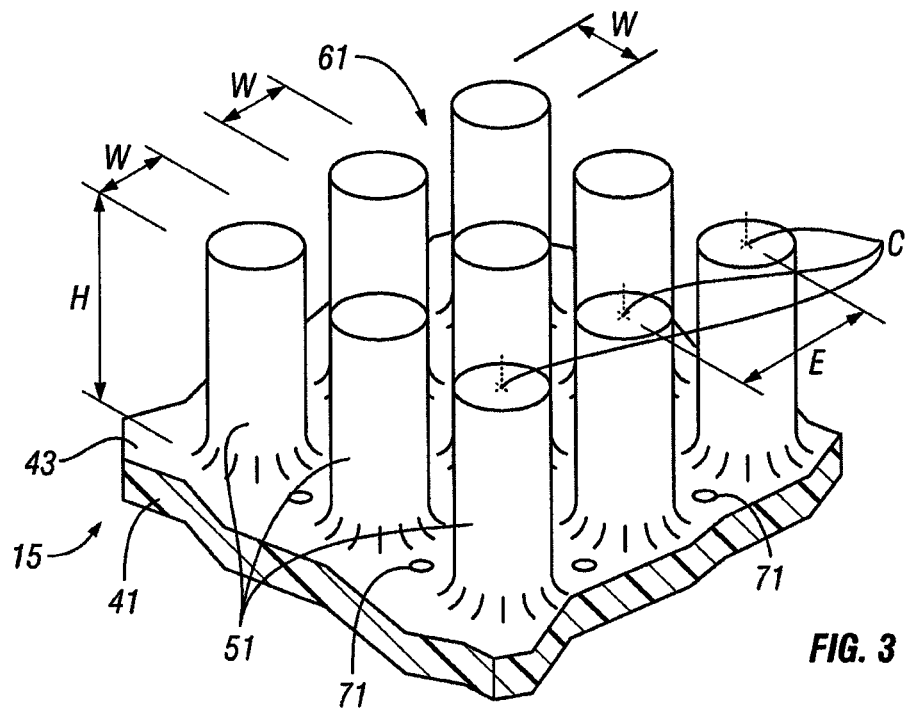
FIG. 3 illustrates the shape of the protrusions of the distribution manifold according to an embodiment of the present invention.

Referring to FIGS. 2 and 3, the distribution manifold 15 is particularly well suited to promote tissue growth at the tissue site 31 yet prevent in-growth of new tissue into the distribution manifold 15. The distribution manifold 15 includes a backing substrate 41 with a tissue contact surface 43. The tissue contact surface 43 preferably includes a plurality of projections, or protrusions 51 that extend from the backing substrate 41. As more specifically shown in FIG. 3, the shape of the protrusions 51 may be substantially cylindrical in shape. Alternatively, the cross-sectional shape of the protrusions 51 may be square, rectangular, triangular, polygonal, elliptical, or any other shape. The protrusions 51 may be tapered or of uniform cross-sectional area throughout.

Referring more specifically to FIG. 3, the height, H, of the protrusions 51 is preferably between about 0.1 and 5.0 millimeters, and more preferably about 2 millimeters. The width, W, of each protrusion is between about 0.1 and 2.0 millimeters, and more preferably about 0.25 to 0.5 millimeters. The width of the protrusions 51 illustrated in FIG. 3 equals that of the diameter since the cross-sectional shape of each protrusion 51 is circular. If the protrusions 51 are square in cross-sectional shape, the width of the protrusions 51 are an edge length of the square. For other cross-sectional shapes, the width is the average of the longest lateral distance through the centroid, C, of the cross section and the shortest lateral distance through the centroid of the cross section. The lateral, center-to-center spacing, E, between each protrusion 51 is preferably between about 0.1 and 1.0 millimeters, and more preferably about 0.5 millimeters. The spacing of the protrusions 51 create distribution channels 61 through which reduced pressure may be delivered to the tissue site 31 and exudates withdrawn from the tissue site 31. It is generally preferred that the height of the protrusions 51 be greater than the width of the protrusions 51. More specifically, the ratio of height to width, H:W, should be greater than about 1:1, and more preferably greater than about 2:1.

The shape, sizing, and spacing of the protrusions 51 may vary depending upon the particular tissue site 31 being treated, the type of material from which the protrusions 51 and backing substrate 41 are made, and the amount of reduced pressure being applied to the tissue site 15. For example, for tissue sites that are highly exudating, it may be advantageous to position the protrusions farther apart to maintain adequate distribution channels 61 between the protrusions 51. In one embodiment of the present invention, the shape, sizing and spacing of the protrusions 51 is uniform for a particular distribution manifold 15. In other embodiments, the shape, sizing, and spacing of the protrusions 51 may vary. For example, protrusions 51 having different cross-sectional shapes may be disposed on the backing substrate 41. Similarly, the sizing and spacing of the protrusions 51 may vary to supply selected portions of the tissue site 31 with more or less reduced pressure.

The presence and sizing of the protrusions 51 allow the protrusions 51 to distribute reduced pressure to the tissue site 31, but prevent new tissue that grows at the tissue site 31 from attaching to the protrusions 51 of the distribution manifold 15. By eliminating the pores or cells that are typically used to deliver reduced pressure to a tissue site, new tissue is not able to wrap around the walls that form the pores or cells. While new tissue growth will grow into the field of protrusions 51 and may even wrap around some of the protrusions 51, the new tissue is not capable of securing itself to the protrusions 51 since the base of each protrusion is anchored to the backing substrate 41.

In addition to distributing reduced pressure to the tissue site 31, the distribution manifold 15 also serves to impart stresses and strains to the tissue site 31 similar to those seen with cellular foam that traditionally has been used in reduced pressure systems. Other materials sometimes used in reduced pressure systems as distribution manifolds, such as gauze, do not have this effect on tissue. The stresses and strains created by the distribution manifold 15 are believed to cause microdeformation of existing tissue and plays a significant role in the generation of new tissue at the tissue site. The amount of stress and strain imparted to a tissue site is determined by the amount of reduced pressure supplied to the tissue site and the surface morphology of the manifold that contacts the tissue site. As reduced pressure is applied, portions of the tissue site are pulled against the distribution manifold 15, and more particularly against the protrusions 51, which results in the development of stresses and strains within the tissue. The sizing of the protrusions 51 on a scale similar to that of the pores of the cellular foam is believed to be one reason for the development of stresses and strains that are similar to those seen with use of the foam.

In one embodiment, the backing substrate 41 is formed from the same material as the protrusions 51. Preferably, that material is silicone or another medical grade material that is relatively impermeable to fluid flow. Alternatively, the material may be a semi-permeable material that allows select fluids or amounts of fluids to pass. The backing substrate 41 may include a plurality of apertures 71 that allow distribution from a surface of backing substrate 41 opposite the protrusions 51 to the tissue contact surface 43 from which the protrusions 51 extend. Since the presence of the apertures 71 could have the same effect on tissue in-growth as that of pores, it is important that the backing substrate 41 and protrusions 51 be removed from the tissue site 31 prior to any new tissue advancing into the apertures 71. In practice, this may be accomplished by knowing the approximate rate of tissue growth, the height of the protrusions 51, and determining the amount of time likely required for new tissue growth to reach the apertures 71.

While the distribution manifold 15 has primarily been described as including backing substrate 41 and plurality of protrusions 51, the distribution manifold 15 may further include cellular foam or another material that is positioned adjacent to or attached to the surface of the backing substrate 41 opposite the protrusions 51. The use of a cellular foam or other material increases the ability of the reduced pressure conduit 19 or the distribution adapter 35 to deliver and distribute reduced pressure to the backing substrate 41. The protrusions 51 and backing substrate 41 serve as a barrier to new tissue growth entering pores of the cellular foam or other material.

Figure 4:
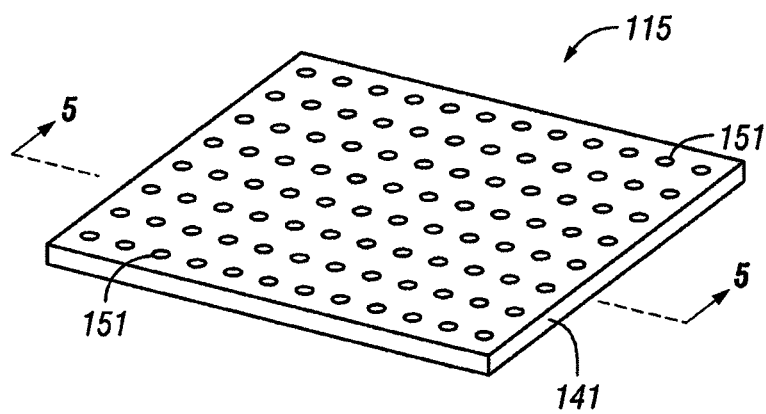
FIG. 4 illustrates a plurality of columnar voids of a distribution manifold according to an embodiment of the present invention.
Figure 5:
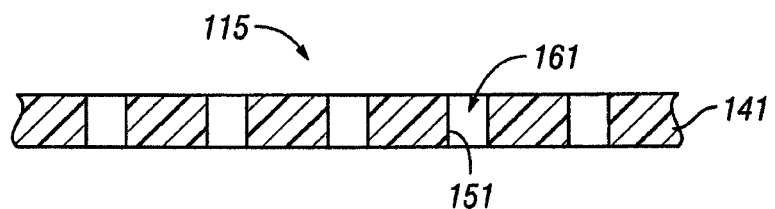
FIG. 5 illustrates a plurality of columnar voids of a distribution manifold according to an embodiment of the present invention.

Referring to FIGS. 4 and 5, a distribution manifold 115 according to another embodiment of the present invention is illustrated. Instead of a plurality of protrusions such as those of distribution manifold 15, distribution manifold 115 includes a plurality of columnar voids 151 formed or otherwise positioned within a backing substrate 141. The term columnar is not meant to imply any particular cross-sectional shape, since the shape of the voids may be any shape as described previously with reference to protrusions 51. Rather, the term columnar refers to the voids generally being greater in length than in width. The voids 151 themselves create a plurality of distribution channels 161 that may be joined by a main channel at an end of the distribution channels 161 opposite that of a tissue site. Alternatively, the distribution channels 161 may simply be apertures that pass completely through the backing substrate 141.

The shape and size of the voids 151 may be similar to that of the protrusions 51 of manifold 15. As previously described, a cellular foam, distribution adapter, or other manifolding device may be placed in fluid communication with the distribution channels 161 to deliver reduced pressure to the tissue site.

Exemplary Distribution Manifold Having Protrusions

Figure 6:
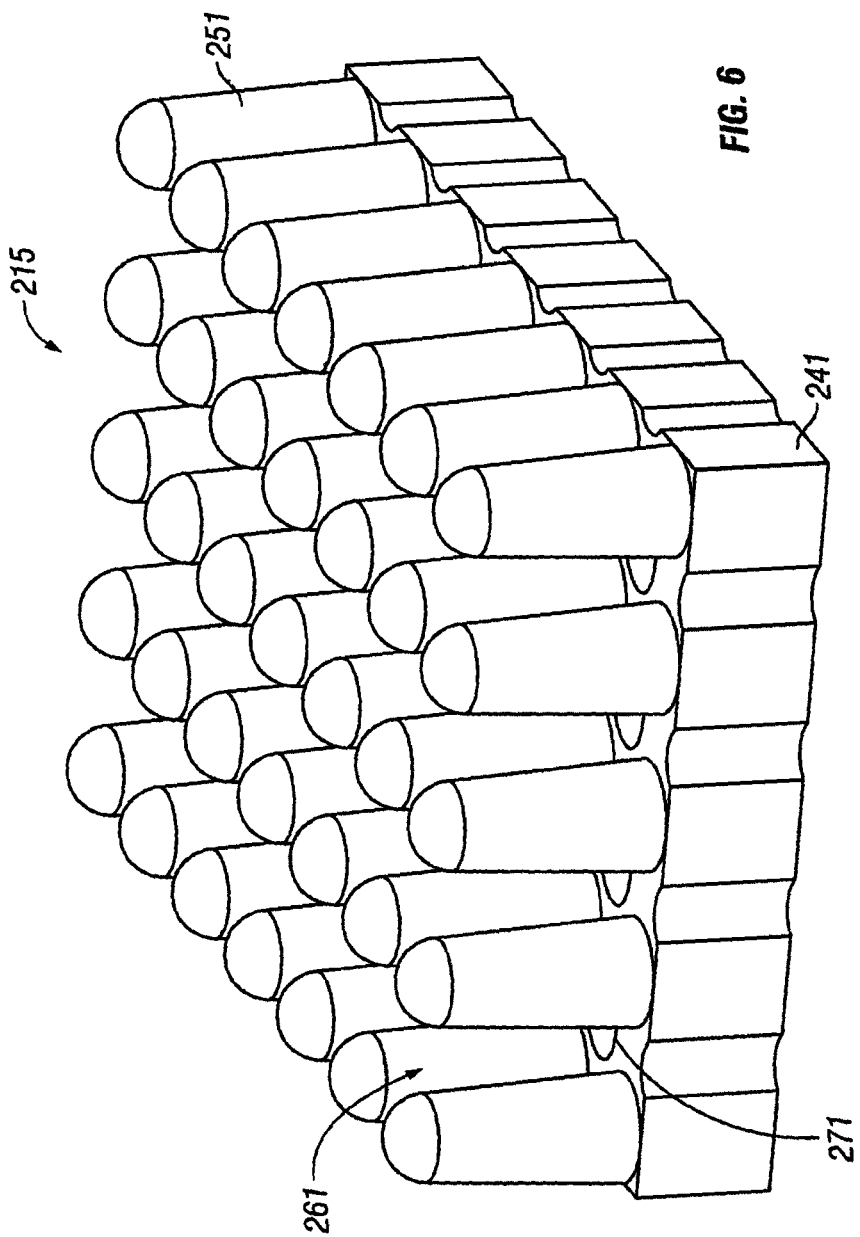
FIG. 6 illustrates a backing substrate with circular protrusions according to an embodiment of the present invention.
Figure 7:
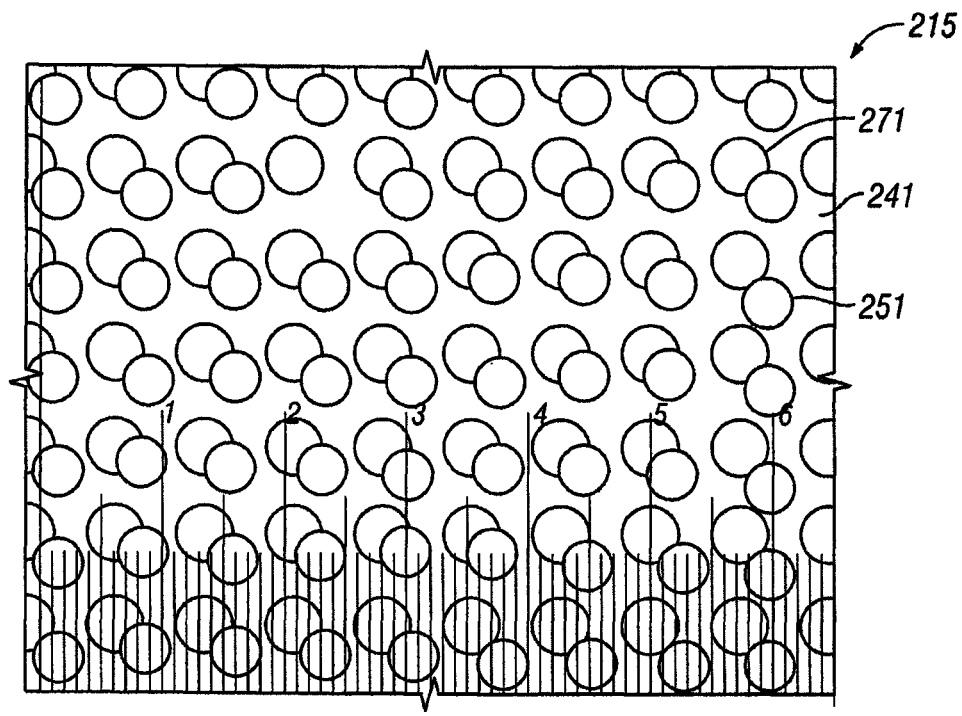
FIG. 7 represents an illustrated reproduction of a photograph of a distribution manifold taken through a microscope according to an embodiment of the present invention.

Referring to FIGS. 6 and 7, one particular distribution manifold 215 that has been tested and that has demonstrated growth induction rates similar to those of cellular foam utilizes a two inch diameter backing substrate 241. The backing substrate includes a plurality of protrusions 251 that are generally circular in cross-sectional shape and tapered inward from the base at which the protrusions meet the backing substrate 241. A plurality of apertures 271 are provided in the backing substrate 241 to allow fluid communication with distribution channels 261 between the protrusions 251. The apertures 271 are disposed in rows and columns that are positioned between the rows and columns of the protrusions 251. The positioning of the apertures 271 in this pattern results in one aperture 271 being centered between every four adjacent protrusions 251 that are arranged in a square pattern (see FIG. 6).

The sizing of the protrusions 215 is such that on the two inch diameter backing substrate 241, approximately 7500 protrusions are present. The width of each protrusion at the base is about 0.5 mm, the height of each protrusion is about 1.5 mm, and the lateral center-to center spacing between the protrusions is about 0.75 mm. The ratio of height to width of the protrusions is about 3:1, and the ratio of the spacing to width is about 1.5:1. The tapering of each protrusion 51 is about a five degree draft angle from the longitudinal axis of the protrusions 51 to aid in molding the distribution manifold 215.

Distribution manifold 215 was sized based on an expected rate of tissue growth and the desired period of use between changes of the distribution manifold 215. For reduced pressures of about 125 mm Hg, one to two millimeters of tissue growth may be expected over a 48 hour period. Since it is desired to change the distribution manifold 215 every 48 hours, a protrusion height of about 1.5 mm allows the majority of the spacing between the protrusions 251 to fill with new tissue growth between dressing changes, but prevents the tissue from attaching to the distribution manifold 251.

Referring more specifically to FIG. 7, an illustrated reproduction of a photograph of the distribution manifold 215 taken through a microscope is provided. The photograph illustrates a top view of the distribution manifold 215 showing the protrusions 251 extending from the backing substrate 241. Also illustrated are apertures 271 disposed between the protrusions 251.

Exemplary Distribution Manifold Having Voids

Figure 8:
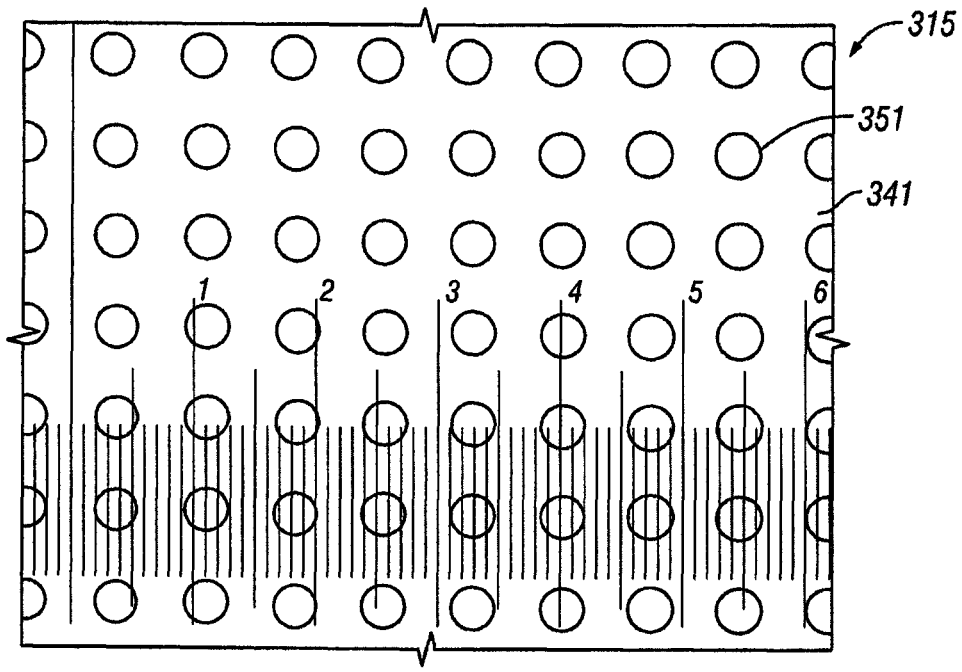
FIG. 8 represents an illustrated reproduction of a photograph of an exemplar distribution manifold having a plurality of columnar voids disposed in a backing substrate according to an embodiment of the present invention.

Referring to FIG. 8, an illustrated reproduction of a photograph of an exemplar distribution manifold 315 having a plurality of columnar voids 351 disposed in a backing substrate 341 is provided. The backing substrate 341 is about 1.5 mm thick, and the width (diameter) of each void 351 is about 0.35 mm. Since the voids 351 extend through the backing substrate 341, the height of each void 351 is about 1.5 mm. The lateral center-to-center spacing between the voids 351 is about 0.75 mm. The ratio of height to width of the voids is about 4.3:1, and the ratio of the spacing to width is about 2.1:1.

It should be apparent from the foregoing that an invention having significant advantages has been provided. While the invention is shown in only a few of its forms, it is not just limited but is susceptible to various changes and modifications without departing from the spirit thereof.

We claim:

1. A reduced pressure treatment system for delivering a reduced pressure to a tissue site comprising:
   a distribution manifold including a backing substrate having a first side adapted to face a tissue site, a second side opposite the first side, and a plurality of protrusions extending from the first side of the backing substrate, wherein the plurality of protrusions have a substantially circular cross-sectional shape having a width between about 0.1 and 2.0 millimeters and a height greater than the width, and wherein the backing substrate has a plurality of apertures formed between the first side and the second side to allow fluid communication between the first side and the second side; and
   a reduced pressure source adapted to be fluidly connected to the apertures on the second side and configured to deliver reduced pressure through the apertures to the first side between the protrusions and to the tissue site;
   whereby the protrusions maintain a specific height to width ratio that prevents new tissue growth from attaching to the distribution manifold.

2. The reduced pressure treatment system of claim 1, wherein a lateral center-to-center spacing of the protrusions is between about 0.1 and 0.5 millimeters.

3. The reduced pressure treatment system of claim 1, wherein a ratio of the height to diameter of the protrusions is 2:1.

4. The reduced pressure treatment system of claim 1, wherein the protrusions are made from medical grade silicone.

5. A reduced pressure treatment system for delivering a reduced pressure to a tissue site comprising:
   a distribution manifold including a backing substrate having a first side adapted to face a tissue site, a second side opposite the first side, and a plurality of protrusions extending from the first side of the backing substrate, wherein the plurality of protrusions have a substantially polygonal cross-sectional shape having a width between about 0.1 and 2.0 millimeters and a height greater than the width, and wherein the backing substrate has a plurality of apertures formed between the first side and the second side to allow fluid communication between the first side and the second side; and
   a reduced pressure source adapted to be fluidly connected to the apertures on the second side and configured to deliver reduced pressure through the apertures to the first side between the protrusions and to the tissue site;
   whereby the protrusions maintain a specific height to width ratio that prevents new tissue growth from attaching to the distribution manifold.

6. The reduced pressure treatment system of claim 5, wherein a lateral center-to-center spacing of the protrusions is between about 0.1 and 0.5 millimeters.

7. The reduced pressure treatment system of claim 6, wherein a ratio of the height of the protrusions to the width of the protrusions is 2:1.

8. The reduced pressure treatment system of claim 5, wherein the protrusions are made from medical grade silicone.

9. A reduced pressure treatment system for delivering a reduced pressure to a tissue site comprising:
   a distribution manifold including a backing substrate having a first side adapted to face a tissue site, a second side opposite the first side, and a plurality of columnar voids extending from the first side of the backing substrate, wherein the plurality of columnar voids have a substantially polygonal cross-sectional shape having a width between about 0.1 and 2.0 millimeters and a height greater than the width, and wherein the backing substrate has a plurality of apertures formed between the first side and the second side to allow fluid communication between the first side and the second side; and
   a reduced pressure source adapted to be fluidly connected to the apertures on the second side and configured to deliver reduced pressure through the apertures to the first side between the columnar voids and to the tissue site;
   whereby the columnar voids maintain a specific height to width ratio that prevents new tissue growth from attaching to the distribution manifold.

10. The reduced pressure treatment system of claim 9, wherein a height of the columnar voids is about 1.5 mm.

11. The reduced pressure treatment system of claim 9, wherein the backing substrate is about 1.5 mm thick.

12. The reduced pressure treatment system of claim 9, wherein the columnar voids completely pass through the backing substrate.

13. The reduced pressure treatment system of claim 9, wherein a lateral center-to-center spacing between the plurality of columnar voids is about 0.75 mm.

14. The reduced pressure treatment system of claim 9 wherein:
   the columnar voids create a plurality of distribution channels that are joined to a main channel at an end of the distribution channels; and
   a reduced pressure source is fluidly connected to the distribution channels of the backing substrate to deliver the reduced pressure to the tissue site.

15. The reduced pressure treatment system of claim 14, further comprising a cellular foam positioned adjacent to the plurality of distribution channels.

16. The reduced pressure treatment system of claim 9, wherein the plurality of columnar voids are square, rectangular, triangular, polygonal, or elliptical shaped.

17. The reduced pressure treatment system of claim 9, wherein the plurality of columnar voids are tapered.

* * * * *